United States Patent [19]

Hanson et al.

[11] Patent Number: 5,411,954

[45] Date of Patent: May 2, 1995

[54] BENZO-FUSED OXAZOPINYL-TERMINATED ALKYLAMINO ETHYNYL ALANINE AMINO DIOL COMPOUNDS FOR TREATMENT OF HYPERTENSION

[75] Inventors: Gunnar J. Hanson, Skokie, Ill.; Robert E. Manning, St. Louis, Mo.

[73] Assignee: G. D. Searle & Co., Chicago, Ill.

[21] Appl. No.: 199,410

[22] Filed: Feb. 22, 1994

Related U.S. Application Data

[62] Division of Ser. No. 930,069, Aug. 14, 1992.

[51] Int. Cl.$^6$ ............... C07D 267/14; A61K 31/55
[52] U.S. Cl. ............................ 514/211; 540/491; 540/552
[58] Field of Search ............... 514/18, 19, 211; 540/552, 491

[56] References Cited

U.S. PATENT DOCUMENTS

| | | | |
|---|---|---|---|
| 4,902,706 | 2/1990 | Hanson et al. | 514/400 |
| 5,032,577 | 7/1991 | Fung et al. | 514/18 |
| 5,212,185 | 5/1993 | Hanson | 514/331 |

FOREIGN PATENT DOCUMENTS

| | | |
|---|---|---|
| 128762 | 12/1984 | European Pat. Off. |
| 181110 | 5/1986 | European Pat. Off. |
| 186977 | 7/1986 | European Pat. Off. |
| 189203 | 7/1986 | European Pat. Off. |
| 200406 | 12/1986 | European Pat. Off. |
| 216539 | 4/1987 | European Pat. Off. |
| 229667 | 7/1987 | European Pat. Off. |
| 300189 | 1/1989 | European Pat. Off. |
| 0307837 | 3/1989 | European Pat. Off. |
| 0310918 | 4/1989 | European Pat. Off. |
| 410260 | 1/1991 | European Pat. Off. |
| 0416393 | 3/1991 | European Pat. Off. |
| 0427939 | 5/1991 | European Pat. Off. |
| 0438233 | 7/1991 | European Pat. Off. |
| 456185 | 11/1991 | European Pat. Off. |
| 87/04349 | 7/1987 | WIPO |
| WO92/22313 | 12/1992 | WIPO |

OTHER PUBLICATIONS

Umezawa et al, in *J. Antibiot.* (Tokyo), 23, pp. 259–262, (1970).
Gross et al, *Science*, 175, p. 656, (1971).
Boger et al, *Nature*, 303, (1983), pp. 81–84.
Kokubu et al, *Biochm. Biophys. Res. Commun.*, 118, pp. 929–933, (1984).
Fehrentz et al, *FEBS Lett.*, 167, (1984), pp. 273–276.
Hanson et al, *Biochm. Biophys. Res. Comm.*, 132, pp. 155–161, (1985).
Hanson et al, *Biochm. Biophys. Res. Comm.*, 145, pp. 959–963, (1987).

*Primary Examiner*—Joseph Paul Brust
*Attorney, Agent, or Firm*—J. Timothy Keane

[57] ABSTRACT

Compounds characterized generally as benzo-fused oxazopinyl-terminated alkylamino ethynyl alanine amino diol derivatives are useful as renin inhibitors for the treatment of hypertension. Compounds of particular interest are those of Formula I $$B\text{---}(\phantom{x})_n\text{---}N\underset{R_1}{\overset{}{|}}\text{---}A\text{---}X\text{---}\underset{R_2}{\overset{}{\underset{|}{C}}}\text{---}\underset{O}{\overset{O}{\underset{\|}{C}}}\text{---}\underset{R_4}{\overset{R_3}{\underset{|}{N}}}\text{---}\underset{R_5}{\overset{}{\underset{|}{N}}}\text{---}\underset{OH}{\overset{R_6\ OH}{\underset{|}{C}}}\text{---}R_7 \quad (I)$$

wherein A is selected from CO and $SO_2$; wherein X is selected from oxygen atom and methylene; wherein B is a benzo-fused oxazopinyl group; wherein $R_1$ is selected from hydrido, methyl, ethyl, isopropyl and n-propyl; wherein $R_2$ is phenylmethyl; wherein each of $R_3$ and $R_5$ is hydrido; wherein $R_4$ is selected from $$-(CH_2)_q-C\equiv C-V$$

wherein V is selected from hydrido and methyl; wherein $R_6$ is cyclohexylmethyl; wherein $R_7$ is selected from isobutyl, cyclopropyl and cyclopropylmethyl; wherein q is a number selected from zero through three, inclusive; and wherein n is a number selected from zero through three, inclusive; or a pharmaceutically-acceptable salt thereof.

14 Claims, No Drawings

BENZO-FUSED OXAZOPINYL-TERMINATED ALKYLAMINO ETHYNYL ALANINE AMINO DIOL COMPOUNDS FOR TREATMENT OF HYPERTENSION

RELATED APPLICATION

This is a divisional of U.S. application Ser. No. 930,069, filed Aug. 14, 1992.

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23, 259–262 (1970)]. This peptide known as pepstatin, was found to reduce blood pressure in vivo after the injection of hog renin into nephrectomized rats [Gross et al, *Science*, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim. Biophys, Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glyco-containing compounds as renin inhibitors [also see Hanson et al, *Biochm. Biophys. Res. Comm.*, 132,155–161 (1985), 146, 959–963 (1987)]. EP Appl. #181,110, published May 14, 1986, describes dipeptide histidine derivatives as renin inhibitors. EP Appl. #186,977 published Jul. 9, 1986 describes renin-inhibiting compounds containing an alkynyl moiety, specifically a propargylglycine moiety, attached to the main chain between the N-terminus and the C-terminus, such as N-[4(S)-[(N)-bis(1-naphthylmethyl)acetyl]-DL-propargylglycyiamino]-3(S) -hydroxy-6-methylheptanoyl]-L-isoleucinol. EP Appl. #189,203, published 30 July 1986, describes peptidyl-aminodiols as renin inhibitors. EP Appl. #200,406, published Dec. 10, 1986, describes alkylnaphthylmethylpropionyl-histidyl aminohydroxy alkanoates as renin inhibitors. EP Appl. #216,539, published Apr. 1, 1987, describes alkylnaphthylmethylpropionyl aminoacyl aminoalkanoate compounds as renin inhibitors orally administered for treatment of renin-associated hypertension. EP Appl. #229,667, published Jul. 22, 1987, describes acyl α-aminoacyl aminodiol compounds having a piperazinylcarbonyl or an alkylaminoalkylcarbonyl terminal group at the N-amino acid terminus, such as 2(S)-([(1-piperazinyl)carbonyl]-oxy]-3-phenylpropionyl)-Phe-His amide of 2(S)-amino-1-cyclohexyl-3(R), 4(S)-dihydroxy-6-methylheptane. PCT Application No. WO 87/04349, published Jul. 30, 1987, describes aminocarbonyl aminoacyl hydroxyether derivatives having an alkylamino-containing terminal substituent and which are described as having renin-inhibiting activity for use in treating hypertension. EP Appl. #300,189 published Jan. 25, 1989 describes amino acid monohydric derivatives having an alkylamino-alkylamino N-terminus and a β-alanine-histidine or sarcosyl-histidine attached to the main chain between the N-terminus and the C-terminus, which derivatives are mentioned as useful in treating hypertension. U.S. Pat. No. 4,902,706 which issued Feb. 13, 1990 describes a series of histidineamide-containing amino alkylaminocarbonyl-H-terminal aminodiol derivatives for use as renin inhibitors. U.S. Pat. No. 5,032,577 which issued Jul. 16, 1991 describes a series of histidineamide-aminodiol-containing renin inhibitors.

Heterocyclic-terminated aminodiol compounds have been described as renin inhibitors. For example, EP #410,260 published Jan. 30, 1991 describes a series of heterocyclic-terminated peptidyl aminodiol renin inhibitor compounds having utility as antihypertensive agents, wherein specific compounds are described having various terminal heterocyclic groups such as morpholino, pyridinyl, piperazinyl, imidazolyl, pyrazolyl and indolyl groups, including the compound (2R -2-benzyl-3-[(2-morpholin-4-ylethyl) methylaminocarbonyl]propionyl-L-(4-thiazolyl)Ala amide of (2S,3R,4S)-2-amino-1-cyclohexyl-3,4-dihydroxy-6-methylheptane. EP #456,185 published Nov. 13, 1991 describes a series of heterocyclic-terminated sulfonamide-containing peptidyl aminodiol renin inhibitor compounds having utility as antihypertensive agents, wherein specific compounds are described having various terminal heterocyclic groups such as piperazinyl, oxo-substituted piperazinyl and morpholino groups.

DESCRIPTION OF THE INVENTION

Morpholino/thiomorpholino-terminated alkylamino ethynyl alanine amino diol compounds, having utility as renin inhibitors for treatment of hypertension in a subject, constitute a family of compounds of general Formula I:

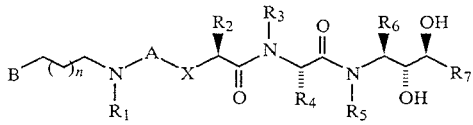

(I)

wherein A is selected from CO and SO₂; wherein X is selected from oxygen atom and methylene; wherein $R_1$ is selected from hydrido and alkyl; wherein B is a saturated heterocyclic ring system of four to ten ring members containing one nitrogen atom and one other heteroatom selected from oxygen atom and sulfur atom as ring members, wherein said ring system may be monocyclic or bicyclic and may be fused to a benzene or cyclohexane ring, wherein the point of attachment of B to the backbone of the structure of Formula I may be through a bond to any substitutable position on said heterocyclic ring system of B and wherein any substitutable position of B may be optionally substituted with one or more radicals selected from alkyl, alkoxy, alkenyl, alkynyl, halo, trifluoromethyl, oxo, cyano and phenyl, and wherein the said heterocyclic ring nitrogen atom may be combined with oxygen to form an N-oxide; wherein R: is selected from alkyl, cycloalkylalkyl, acylaminoalkyl, phenylalkyl and naphthylalkyl, and wherein the cyclic portion of any of said phenylalkyl, cycloalkylalkyl and naphthylalkyl groups may be substituted by one or more radicals selected from halo, hydroxy, alkoxy and alkyl; wherein each of $R_3$ and $R_5$ is independently selected from hydrido and alkyl; wherein $R_4$ is selected from

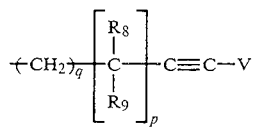

wherein V is selected from hydrido, alkyl, benzyl and phenyl; wherein each of $R_8$ and $R_9$ is a radical independently selected from hydrido, alkyl, alkenyl and phenyl; wherein $R_6$ is selected from alkyl, cycloalkylalkyl and phenylalkyl, any one of which may be substituted with one or more groups selected from alkyl, hydroxy and alkoxy; wherein $R_7$ is selected from hydrido, alkyl, cycloalkyl, cycloalkylalkyl, hydroxyalkyl and alkenyl; wherein p is a number selected from zero through five, inclusive; wherein q is a number selected from zero through five, inclusive; and wherein n is a number selected from zero through five, inclusive; or a pharmaceutically-acceptable salt thereof.

A preferred family of compounds consists of compounds of Formula I wherein A is selected from CO and SO₂; wherein X is selected from oxygen atom and methylene; wherein $R_6$ is selected from hydrido and alkyl; wherein B is a saturated heterocyclic ring system of four to ten ring members containing one nitrogen atom and one other heteroatom selected from oxygen atom and sulfur atom as ring members, wherein said ring system may be monocyclic or bicyclic and may be fused to a benzene or cyclohexane ring, wherein the point of attachment of B to the backbone of the structure of Formula I may be through a bond to any substitutable position on said heterocyclic ring system of B and wherein any substitutable position of B may be optionally substituted with one or more radicals selected from alkyl, alkoxy, alkenyl, alkynyl, halo, trifluoromethyl, oxo, cyano and phenyl, and wherein the said heterocyclic ring nitrogen atom may be combined with oxygen to form an N-oxide; wherein $R_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of $R_3$ and $R_5$ is independently selected from hydrido and methyl; wherein $R_4$ is selected from

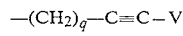

wherein V is selected from hydrido and alkyl; wherein $R_6$ is selected from cyclohexylmethyl and phenylmethyl, either one of which may be substituted with one or more groups selected from alkyl, hydroxy and alkoxy; wherein $R_7$ is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

A more preferred family of compounds consists of compounds of Formula I wherein A is selected from CO and SO₂; wherein X is selected from oxygen atom and methylene; wherein $R_1$ is selected from hydrido, methyl, ethyl, isopropyl and n-propyl; wherein B is a heterocyclic ring system selected from morpholinyl, thiazetidinyl, oxazetidinyl, 2-oxomorpholinyl, thiomorpholinyl, thiazolidinyl, oxazepinyl, oxazocinyl, thiazepinyl, thiazocinyl and 3-oxa-8-azabicyclo[3.2.-1]octanyl and wherein any of said heterocyclic ring systems may be fused to a benzene or cyclohexane ring, wherein the point of attachment of B may be through a bond to any substitutable position on said heterocyclic ring system and where any substitutable position of B may be optionally substituted with one or more radicals selected from alkyl, alkoxy, alkenyl, alkynyl, halo, trifluoromethyl, oxo, cyano and phenyl, and wherein the nitrogen atom ring member of B may be combined with oxygen to form an N-oxide; wherein $R_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydromy, alkoxy and alkyl; wherein each of $R_3$ and $R_5$ is independently selected from hydrido and methyl; wherein $R_4$ is selected from

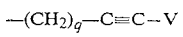

wherein V is selected from hydrido and alkyl; wherein $R_6$ is selected from cyclohexylmethyl and phenylmethyl, either one of which may be substituted with one or more groups selected from alkyl, hydroxy and alkoxy; wherein $R_7$ is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

An even more preferred family of compounds consists of compounds Formula I wherein A is selected from CO and SO₂; wherein X is selected from oxygen atom and methylene; wherein $R_1$ is selected from hydrido, methyl, ethyl, isopropyl and n-propyl; wherein B is a heterocyclic ring system selected from the group consisting of:

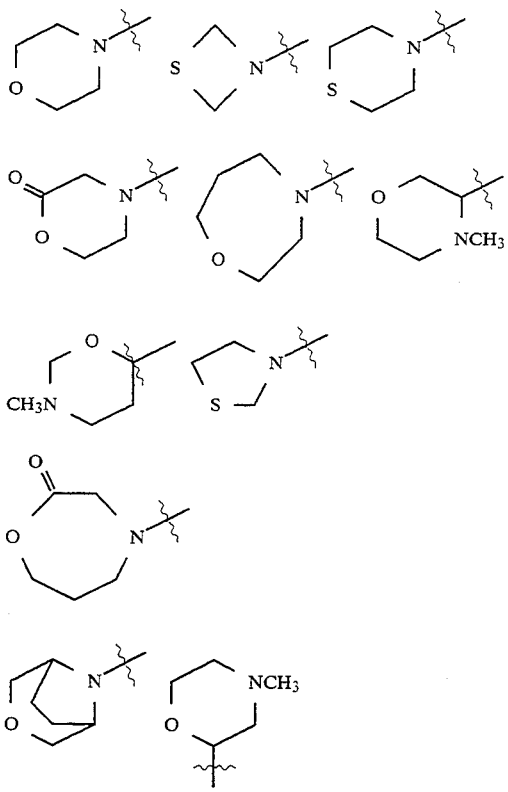

wherein said B group is attached to the backbone of the structure of Formula I through the bond on each B group bisected by the wavy line, and wherein any substitutable position may be optionally substituted with one or more radicals selected from alkyl, alkoxy, alkenyl, alkynyl, halo, trifluoromethyl, oxo, cyano and phenyl, and wherein the nitrogen atom ring member of B may be combined with oxygen to form an N-oxide; wherein $R_2$ is selected from phenylmethyl and wherein the cyclic portion of said phenylmethyl group may be substituted by one or more radicals selected from halo, hydroxy, alkoxy and alkyl; wherein each of $R_3$ and $R_5$ is independently selected from hydrido and methyl; wherein $R_4$ is selected from $$-(CH_2)_q-C\equiv C-V$$

wherein V is selected from hydrido and methyl; wherein $R_6$ is cyclohexylmethyl; wherein $R_7$ is selected from isobutyl, cyclopropyl and cyclopropylmethyl; wherein q is a number selected from zero through three, inclusive; and wherein n is a number selected from zero through three, inclusive; or a pharmaceutically-acceptable salt thereof.

A highly preferred family of compounds consists of compounds of Formula I wherein A is selected from CO and $SO_2$; wherein X is selected from oxygen atom and methylene; wherein $R_1$ is selected from hydrido, methyl, ethyl, isopropyl and n-propyl; wherein $R_2$ is phenylmethyl; wherein each of $R_3$ and $R_5$ is hydrido; wherein $R_4$ is selected from $$-(CH_2)_q-C\equiv C-V$$

wherein V is selected from hydrido and methyl; wherein $R_6$ is cyclohexylmethyl; wherein $R_7$ is selected from isobutyl, cyclopropyl and cyclopropylmethyl; wherein q is a number selected from zero through three, inclusive; and wherein n is a number selected from zero through three, inclusive; or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a >CH— group; or, as another example, two hydrido groups may be attached to a carbon atom to form a —$CH_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "alkoxy" embraces linear or branched oxy-containing radicals having alkyl portions of one to about ten carbon atoms, such as methoxy group. The "alkoxy" radical may be further substituted with one or more halo atoms, such as fluoro, chloro or bromo, to provide haloalkoxy groups. The term "sulfonyl", whether used alone or linked to other terms, denotes the divalent radical $SO_2$. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "alkenylalkyl" denotes a radical having a double-bond unsaturation site between two carbons, and which radical may consist of only two carbons or may be further substituted with alkyl groups which may optionally contain addimional double-bond unsaturation. A group embraced by the term "heterocyclic ring system" may be attached to the backbone of Formula I as a substituent through a carbon atom of the hetero ring system, or may be attached through a carbon atom of a moiety substituted in a hetero ring-member carbon atom. Also, such hetero-containing group may be attached through a ring nitrogen atom. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formula I are isomeric forms, including diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic toluenesulfonic, sulfanilic, mesylic, cyclohexylaminosulfonic, stearic, algenic, $\beta$-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylezhylenediamine, chloroprocaine, choline, diethanolamine, ethylenediamine, meglumine (N-methylglucamine) and procaine. Also included within the phrase "pharmaceutically-acceptable salts" are "quaternary" salts or salts of "onium" cations, such as ammonium, morpholinium and piperazinium cations, as well as any substituted derivatives of these cations where the salt is formed on the nitrogen atom lone pair of electrons. All of these salts may be prepared by conventional means from the corresponding compound of Formula I by reacting, for example, the appropriate acid or base with the compound of Formula I.

Compounds of Formula I would be useful to treat various circulatory-related disorders. As used herein, the term "circulatory-related" disorder is intended to embrace cardiovascular disorders and disorders of the circulatory system, as well as disorders related to the circulatory system such as ophthalmic disorders including glaucoma. In particular, compounds of Formula I would be useful to inhibit enzymatic conversion of angiotensinogen to angiotensin I. When administered orally, a compound of Formula I would be expected to inhibit plasma renin activity and, subsequently, lower blood pressure in a patient such as a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a subject suffering from or afflicted with the effects of hypertension or susceptible to a hypertensive condition if not treated to prevent or control such hypertension. Other examples of circulatory-related disorders which could be treated by compounds of the invention include congestive heart failure, renal failure and glaucoma.

Description of the Synthetic Methods for the Preparation of the Renin Inhibitors of the Invention

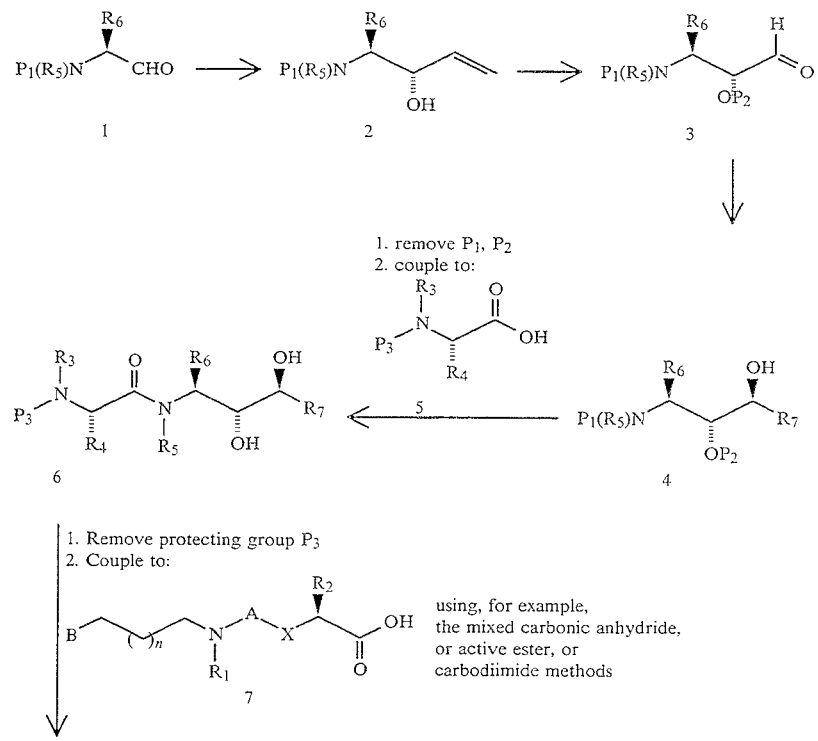

Synthetic Scheme 1

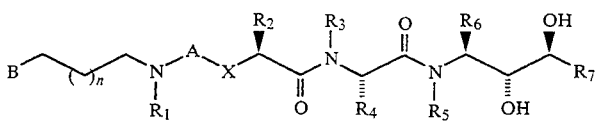

Formula I

Wherein R₁–R₇, X, A, B, and n are as defined before.

Synthetic Scheme 1

Preparation of Compounds of Formula I

A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceeding process is exemplified in Hanson, et al., J. Org. Chem. 50, 5399 (1985). This aldehyde is reacted with an organometallic reagent such as isobutylmagnesium chloride to give intermediate 4. Other suitable organometallic reagents include ethylmagnesium bromide, vinylmagnesium bromide, cyclopropylmagnesium bromide, and allylmagnesium bromide, but the choices are not limited to these reagents. After the formation of 4, further transformation of the added side chain is permitted, before going on the next depicted step. For example, the compound 4 derived from the addition of allylmagnesium bromide may be cyclopropanated via diazomethane and rhodium acetate, to give a cyclopropylmethyl side chain. Compound 4 is deprotected then coupled, using standard amide/peptide coupling methodology to protected triple bond-containing (ethynyl) amino acid derivatives 5 to give compound 6. These standard coupling procedures such as the carbodiimide, active ester (N-hydroxysuccinimide), and mixed carbonic anhydride methods are shown in Benoiton, et al. J. Org. Chem. 48, 2939 (1983) and Bodansky, et al. "Peptide Synthesis", Wiley (1976). Ethynyl-containing amino acid derivatives may be prepared by using procedures such as found in Schollkopf, Tetrahedron 29, 2085 (1982). Intermediate 6 is then deprotected, then coupled to intermediate 7 using the standard amide/peptide coupling methodology, to give compounds of Formula I. Suitable protecting groups may be selected from among those reviewed by R. Geiger in "The Peptides", Academic Press, N.Y. vol. 2 (1979). For example, P₁ and P₃ may be Boc or Cbz; P₂ may be a typical oxygen protective group such as acetyl or t-butyldimethylsilyl.

Synthetic Scheme 2

Preparation of 7:

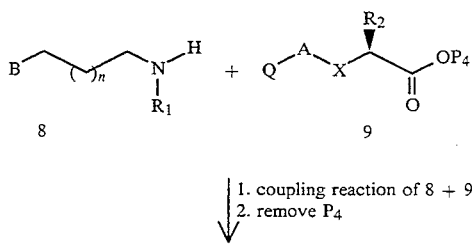

1. coupling reaction of 8 + 9
2. remove P₄

-continued
Synthetic Scheme 2

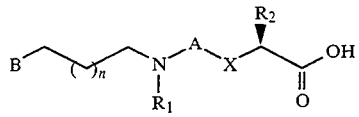

Wherein R₁, R₂, X, A, B and n are as defined before.

Synthetic Scheme 2

Preparation of Compounds of Formula I

Intermediate 7 may be prepared according to the schematic of Synthetic Scheme 2. Intermediate 7 is prepared by coupling the heterocyclicalkylamine 8 to mono-protected carboxylic acid 9. Carboxylic acid or sulfonic acid 9 is a mono-activated moiety by virtue of a suitable leaving group Q which may be chloride, bromide, fluoride, N-hydroxysuccinimido, p-toluenesulfonyloxy or isobutyloxycarbonyloxy, but is not limited to these groups. After coupling, protecting group P₄ is removed (if P₄ is a benzyl group, hydrogenolysis over palladium-on-carbon (Pd-C) is performed) to give intermediate amino acid 7.

Abbreviations used:

P₁ is an N-protecting group; P₂ is H or an oxygen protecting group; P₃ is an N-protecting group; P₄ is an oxygen protecting group such as benzyl or methyl; Q is a leaving group; Boc is t-butyloxycarbonyl; Cbz is carbobenzoxy. The following Steps constitute specific exemplification of methods to prepare starting materials and intermediates embraced by the foregoing generic synthetic scheme. Those skilled in the art will readily understand that known variations of the conditions and processes of the following preparative procedures can be used to prepare the compounds of the Steps. All temperatures expressed are in degrees Centigrade.

Step 1

(2R,3S)-N-[(tert-Butyloxy)carbonyl]-3-amino-2-acetoxy-4-phenylbutanal

Ozone/oxygen was bubbled at −70° C. into a solution of (3S,4S)-N-[(tert-Butyloxy)carbonyl]-4-amino-3-acetoxy-5-phenylpentene (2.55 g, 8.0 mmol) [prepared by the method of Hanson et al., J. Org, Chem., 50, 5399 (1985)] in 100 mL of methylene chloride until a deep blue color persisted. Oxygen was introduced until the blue color completely faded, then 3.0 mL of Me₂S was added and the solution was allowed to warm to 0°–5° C. and stand overnight. The solvent was removed at 0° C. under vacuum yielding the title compound as a thick yellow oil which was used without further purification.

Step 2

(2S,3R,4S)-N-[(tert-Butyloxy)carbonyl]-2-amino-1-phenyl-3,4-dihydroxy-6-methylheptane The title compound of Step 1 was dissolved under nitrogen in 100 mL of dry THF and cooled to −70° C. To this solution was added 13 mL (26mmol) of a 2.0M solution of isobutylmagnesium chloride in ether and the stirred mixture was allowed to warm to room temperature and stir for 2 hrs. After decomposition with MeOH/$H_2O$ the mixture was diluted with ether, washed with saturated $NH_4Cl$ solution twice and dried with magnesium sulfate and the solvents evaporated under vacuum. The residue was allowed to stand overnight in 80% MeOH-$H_2O$ containing excess ammonium hydroxide. The MeOH was stripped off and the mixture was extracted with ether. These extracts were combined, washed with water, dilute $KHSO_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134°–136° C., Rf (ether): single spot, 0.6. By chromatography of the mother liquors and crystallization of the appropriate fractions, an additional 0.22 g of product, mp 138°–139° C., was obtained. Anal: Calcd. for $C_{19}H_{31}NO_4$: C, 67.62; H, 9.26; N, 4.15. Found: C, 67.51; H, 9.43; N, 4.24.

Step 3

(2S,3R,4S)-N-[(tert-Butyloxy)carbonyl]-2-amino-1-cyclohexyl-3,4-dihydroxy-6-methylheptane The title compound of Step 2 (0.27 g) was reduced in MeOH with 60 psi $H_2$ at 60° in 3 hrs using 5% Rh/C catalyst. After filtering, the solvent was stripped off and the white crystals were recrystallized from $CH_2Cl_2$-hexane to furnish tiny needles of the title compound (0.19 g, mp126°–128° C.); further recrystallization gave mp 128.5°–129.5° C. Rf (ether): single spot, 0.8. Anal: Calcd. for $C_{19}H_{37}NO_4$: C, 66.43; H, 10.86, N, 4.08. Found: C, 66.43; H, 11.01; N, 4.03.

Step 4

(2S, 3R, 4S) 2-amino-1-cyclohexyl-3,4-dihydroxy-6-methylheptane

The title compound of Step 3 (10 g) was dissolved 6.9N HCl in dioxane (300 mL). The mixture was stirred for 30 minutes at room temperature. The solvent was removed in vacuo and to the residue was added 5% aqueous sodium hydroxide (30 mL) until a DH of 14 was obtained. This mixture was extracted with ether and the ether extract was washed with water and brine, then the solvent was evaporated to give the title compound (7.3 g, 100% yield). 300 MHz $^1H$ NMR: consistent with proposed structure. Anal. calcd for $C_{14}H_{29}NO_2$: C, 69.07; H, 12.01; N, 5.78. Found: C, 69.19; H, 12.34; N, 5.78.

Step 5

L-Boc-C-propargylglycine

L-C-Propargylglycine (10 g) [prepared by the method of Schwyzer et al., *Helv. Chim. Acta*, 59, 2181 {1976}] was suspended in tetrahydrofuran (30 mL). Water (30 mL), potassium carbonate (36.7 g), and di-tert-butyldicarbonate (21.9 g) were added. Additional water was added to produce a solution which was stirred for 12 hours at room temperature. The organic solvent was then evaporated and the aqueous solution was washed with ether, then acidified to pH 3 with 1N aqueous citric acid. The solution was extracted with methylene chloride and the solvent evaporated to give the title compound (18.9 g, 97% yield), used without further purification.

Step 6

Boc L-C-propargylglycine amide of (2S,3R,4S) 2-amino-1-cyclohexyl-3,4-dihydroxy-6-methylheptane Boc L-C-propargylglycine (1.2 g) was dissolved in methylene chloride (5 mL) and N-methyl piperidine (0.57 g) was added. The mixture was cooled to zero degrees centigrade and isobutyl chloroformate (0.78 g) was added. The mixture was stirred for 10 minutes whereupon the title compound of Step 4 (1.4 g) in methylene chloride (5 mL) was added and this mixture stirred for 15 minutes at 0° C. and 4° C. for 12 hours. The reaction mixture was washed successively with 1N citric acid, saturated sodium hydrogen carbonate, water and brine. The organic layer was dried over magnesium sulfate and evaporated to dryness. The residue was chromatographed on silica gel to give the title compound as a colorless oil. 300 MHz $^1H$ NMR: consistent with proposed structure.

Step 7

L-C-propargylglycine amide of (2S,3R,4S) 2-amino-1-cyclohexyl-3,4-dihydroxy-6-methylheptane The title compound of Step 6 (0.76 g) was dissolved in a mixture of trifluoroacetic acid (4.9 mL) and methylene chloride (4.9 mL), and stirred for 30 minutes at room temperature. The solvent was then evaporated and the residue taken up in ethyl acetate. The organic layer was washed with saturated sodium hydrogen carbonate, water and brine, then dried over magnesium sulfate and evaporated to give the title amine. 300 MHz $^1H$ NMR: consistent with proposed structure.

Step 8

2R-(Phenylmethyl)butanedioic acid, 1-(phenylmethyl) ester, dicyclohexylammonium salt To a slurry of 4-(4-methoxybenzyl)itaconate [prepared by the method of Talley in U.S. Pat. No. 4,939,288] (50 g) in toluene (250 mL) was added 1,8-diazabicyclo[5.4.0]undec-7-ene (DBU, 30.4 g) in one portion. Then a solution of benzyl bromide (34.2 g) in toluene (50 mL) was added dropwise over 0.5 hour. The reaction was stirred for 0.5 hour at room temperature and then poured into a separatory funnel. The mixture was washed with 3N HCl, aqueous sodium bicarbonate, brine and dried over magnesium sulfate. The solvent was evaporated to give a clear mobile liquid (68 g). Chromatography on silica gel, eluting with from 100% hexane to 25% ethyl acetate gave pure 1-(benzyl)-4-(4-methoxybenzyl) itaconate (55 g, 81% yield). A large Fisher-Parter bottle was charged with this itaconate (41 g), triethylamine (36 g), palladium acetate (380 mg), tri-o-tolylphosphine (1.04 g) and iodobenzene (24.7 g). The bottle was sealed and flushed with nitrogen and placed in an oil bath and heated for 70 minutes. The residue was chromatographed on silica gel, eluting with 100% hexanes until the less polar impurities were removed. Eluting with 10% ethyl acetate in hexane gave the pure phenyl itaconate. This compound (23.8 g) was mixed with toluene (200 mL) and the resulting solution treated with trifluoroacetic acid (30 mL). The solution was stirred an room temperature for 1.5 hour and then evaporated. The residue was taken up in ether (150 mL) and treated with dicyclohexylamine (10.4 g) and stirred at 0° whereupon the salt precipitated. This was isolated by filtration and washed with hexane and dried to give pure 1-benzyl 2-benzylidene succinoate cyclohexylammonium salt (21.24 g, 78% yield). This benzylidene compound (20 g) was place in a Fisher-Porter bottle and also added were degassed methanol (200 mL) and rhodium (R,R) DiPAMP (600 mg) catalyst. The bottle was sealed and flushed with nitrogen then hydrogen. The reaction was hydrogenated at 40 psig for 15 hours at room temperature. The contents were then poured into a round bottom flask (500 mL) and the solvent evaporated to give a dark solid. The residue was taken up in boiling isooctane and allowed to stand, with some title compound crystallizing (7.34 g). The non-dissolved residue was taken up in boiling dimethoxyethane. This solution was allowed to cool for 12 hours, whereupon crystals of the title compound formed (6.05 g). Combining the two crops gave 13.39 g, 66% yield, mp 122°-125°. 300 MHz $^1$H NMR: consistent with proposed structure.

Step 9

2R-(Phenylmethyl)butanedioic acid, 1-(phenylmethyl) ester

The title compound of Step 8 (9.3 g) was suspended in a mixture of water (84 mL) and methanol (8.5 mL). Solid sodium bisulfate (6.12) was added and the mixture stirred for 5 minutes. The mixture was extracted with methylene chloride and the combined extracts were dried over magnesium sulfate and evaporated to dryness. The residue was chromatographed on silica gel, eluting with methanol-chloroform-acetic acid (5:95:0.5), to give the pure title compound (4.3 g, 74% yield).

Step 10

4-[2(N-Formylamino)ethyl]morpholine

The procedure of B. V. Cheney et al. [J. Med, Chem., 28, 1853–1864 (1985)] was used. A solution of 4-(2-aminoethyl)morpholine (1.00 g, 76.8 mmol) and ethyl formate (213 mL, 2640 mmol) was refluxed overnight under an atmosphere of nitrogen. Vacuum distillation gave 11.46 g (100% yield) of a clear, colorless liquid (bp 0.3 118°-120° C.). The 1H NMR spectral data were consistent with the structure of the title compound.

Step 11

4-[2-Methylamino)ethyl]morpholine

A solution of the title compound of Step 10 in anhydrous tetrahydrofuran (50 mL) was added dropwise to a solution of lithium aluminum hydride (8.07 g, 213 mmol) in anhydrous tetrahydrofuran (504 mL) at room temperature. The mixture was refluxed overnight. To the reaction solution was added H20 (8.0 mL), a 15% NaOH solution (8.0 mL), and H$_2$O (24 mL). The filtrate was vacuum distilled to give 4.94 g (72% yield) of the title compound as a clear, colorless liquid (bp$_{10}$ 74°-76° C). The proton and carbon NMR spectral data were consistent with the proposed structure.

Step 12

Phenylmethyl αR-[2-[methyl[2-(4-morpholinyl)ethyl]amino]-2-oxoethyl]benzenepropanoate To a solution of the title compound of Step 9 (0.72 g, 2.43 mmol) and pyridine (0.19 g, 2.43 mmol) in methylene chloride (8 mL) was added N,N'-disuccinimidyl carbonate (DSC, 0.62 g, 2.43 mmol) and dimethylaminopyridine (DMAP, 18 mg). After 3 hours, the title compound of Step 11 (0.35 g, 2.43 mmol) was added and the solution stirred overnight. The reaction mixture was diluted with CH$_2$Cl$_2$ (12 mL) and then was washed with 5% aqueous K$_2$CO$_3$ solution (2×5 mL), H$_2$O (10 mL), and brine (10 mL). The organic layer was dried over MgSO$_4$. The filtrate was concentrated and purified by medium pressure column chromatography (silica gel, 3% MeOH in CHCl$_3$, Rf=0.08) to give 0.925 g (89% yield) of the title compound as an oil. The proton NMR spectral data were consistent for the proposed structure.

Step 13

αR-[2-[methyl[2-(4-moroholinyl)ethyl]amino]-2-oxoethyl]benzenepropanoic acid

A mixture of the title compound of Step 12 (0.632 g, 1.49 mmol) and 4% Pd/C (0.070 g) in EtOH (10 mL) was placed under a hydrogen atmosphere with a balloon for 18 hours. The mixture was filtered through a celite bed. The filtrate was concentrated to give 0.486 g (98% crude yield) of the title compound as a white foam. The proton NMR spectral data was consistent with the proposed structure.

The following working Example is provided to illustrate synthesis of Compounds 1–20 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

EXAMPLE 1

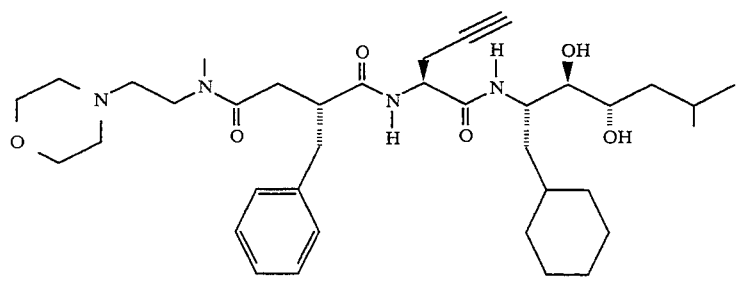

N¹-[1R*-[[[1S,1R*-(cyclohexylmethyl)-2S*,3R*-dihydroxy-5-methylhexyl]amino]carbonyl]-3-butynyl]-N⁴-methyl-N⁴-[2-(4-morpholinyl)ethyl]-2S*-(phenylmethyl)butanediamide The acid of Step 13 (150 mg) was dissolved in methylene chloride (1 mL) at room temperature and pyridine (36 mL) was added, followed by solid N,N'-disuccinimidyl carbonate (114 mg). Dimethylaminopyridine (15 mg) was next added. Gas evolution ensued and ceased after 0.5 hour. After stirring at room temperature for 2 hours, the amine of Step 7 (136 mg) was added as a solid. The reaction mixture was then allowed to stir for 12 hours, whereupon the solvent was evaporated at reduced pressure and the residue was taken up in methanol. To this solution was added 5 drops of 5% aqueous potassium carbonate solution. After the mixture stood for 15 minutes, the methanol was evaporated at reduced pressure and the residue partitioned between ethyl acetate and 5% aqueous potassium carbonate. The organic layer was then washed successively with 5% aqueous potassium carbonate, water and brine and evaporated to a yellow foam (236 mg). This was chromatographed on silica gel, eluting with methylene chloride-methanol (9:1) to give the pure title compound (120 mg, 45% yield) as a white foam. 1H NMR (CDCl₃): consistent with proposed structure. Anal. calcd. for $C_{37}H_{58}N_4O_6$: C, 67.86; H, 8.93; N, 8.56. Found: C, 67.45; H, 9.05; N, 8.36.

Compounds #2–20, as shown in Table I below, may be synthesized by reference to the foregoing specific and general procedures for preparing compounds of Formula I.

TABLE I

| Example Compound No. | Structure |
| --- | --- |
| 2 | 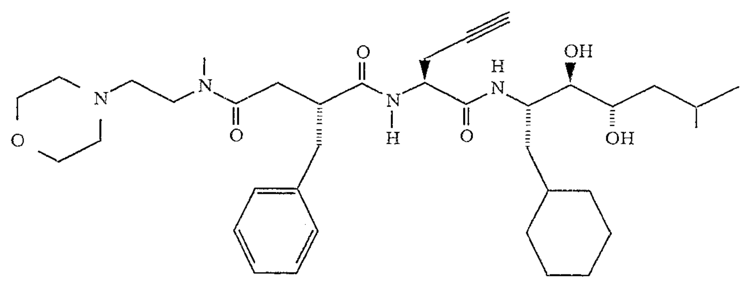 |
| 3 | 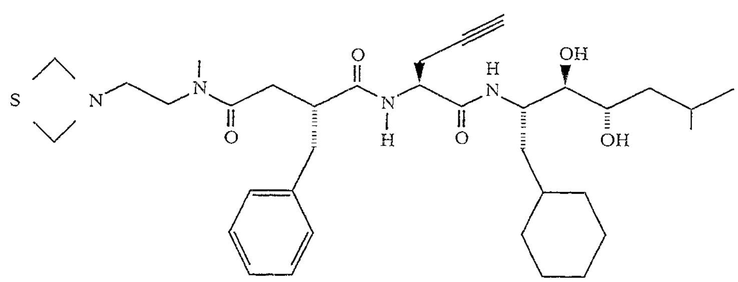 |
| 4 | 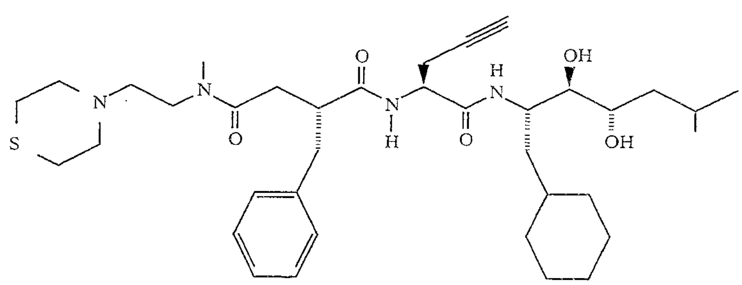 |
| 5 | 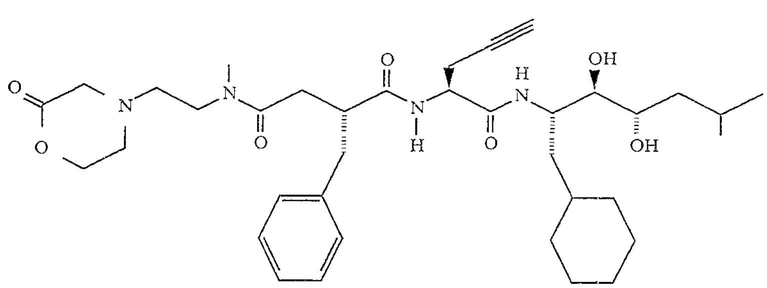 |

TABLE I-continued

| Example Compound No. | Structure |
|---|---|
| 6 | 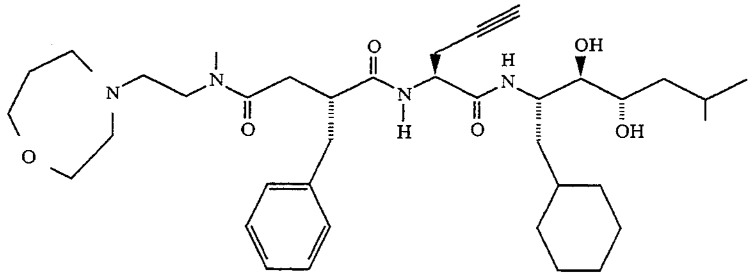 |
| 7 | 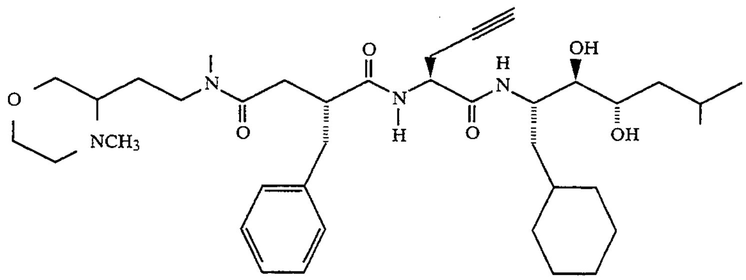 |
| 8 | 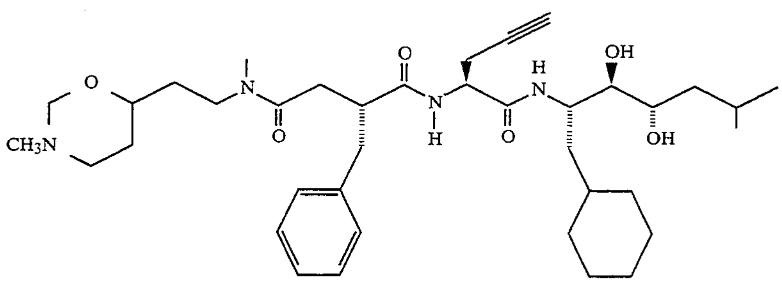 |
| 9 | 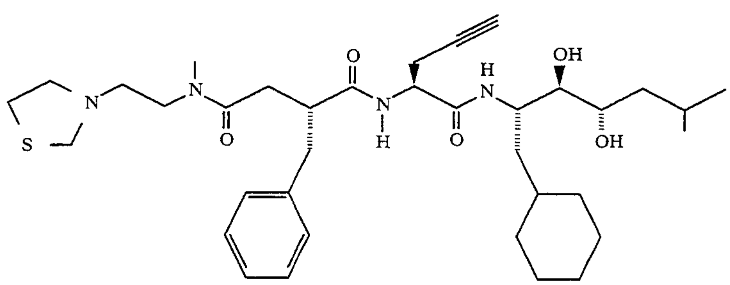 |
| 10 | 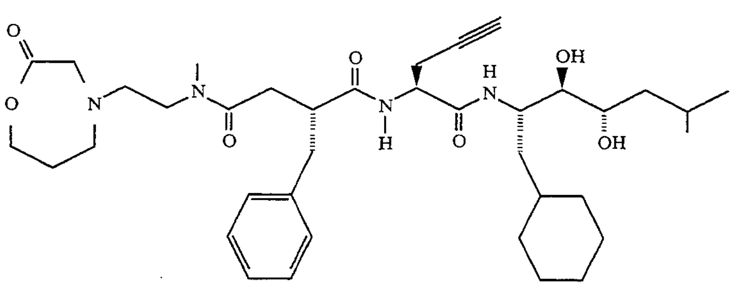 |

TABLE I-continued

| Example Compound No. | Structure |
|---|---|
| 11 | 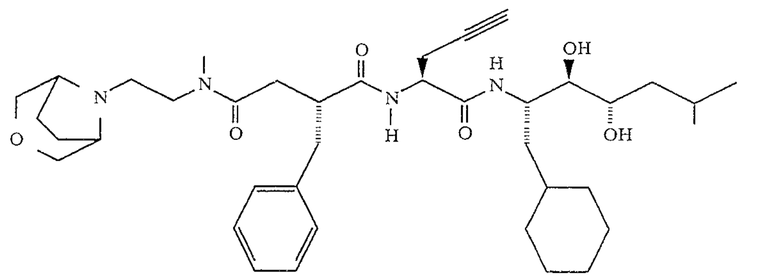 |
| 12 | 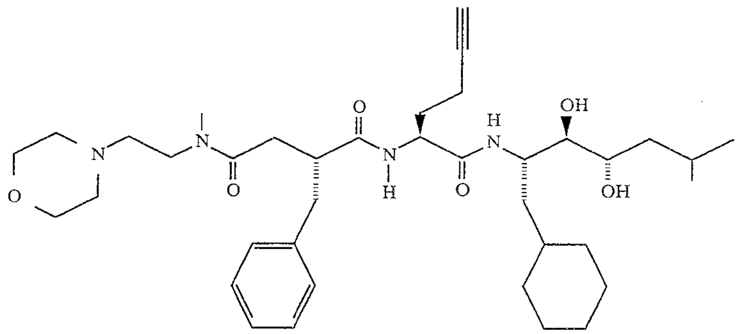 |
| 13 | 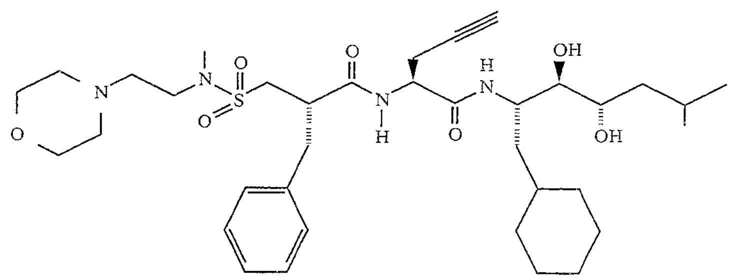 |
| 14 | 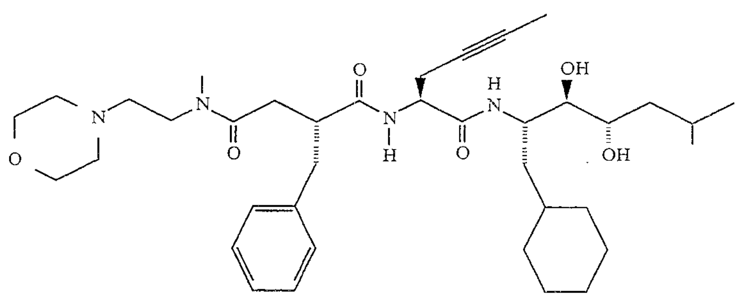 |
| 15 | 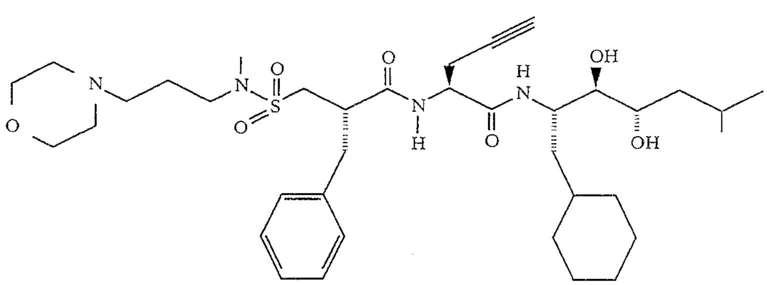 |

TABLE I-continued

| Example Compound No. | Structure |
|---|---|
| 16 | 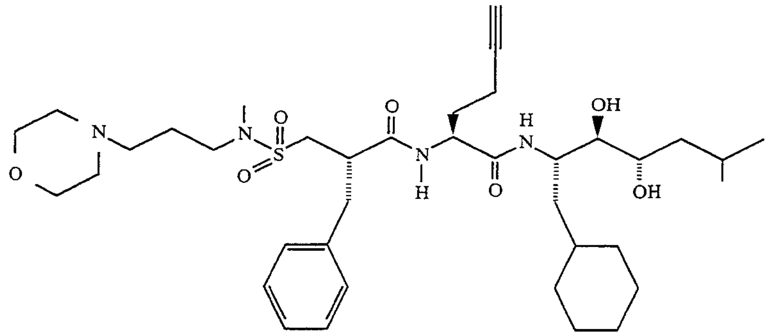 |
| 17 | 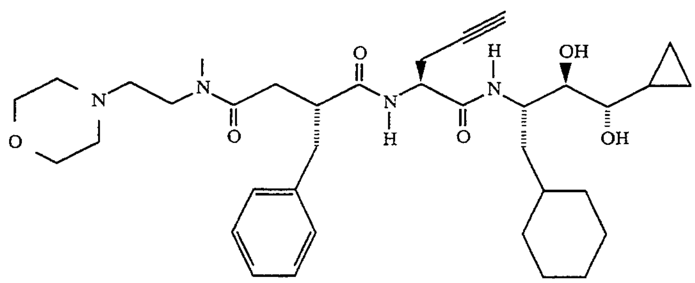 |
| 18 | 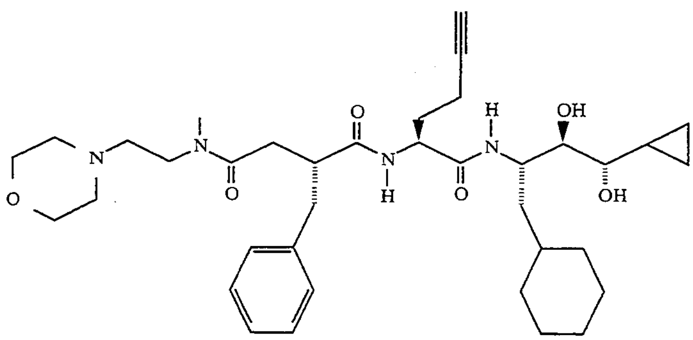 |
| 19 | 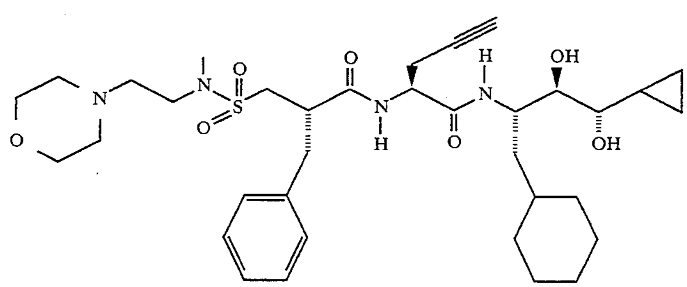 |
| 20 | 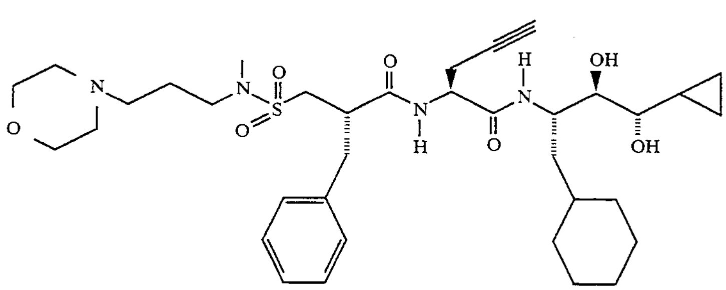 |

TABLE I-continued

| Example Compound No. | Structure |
| --- | --- |
| 21 | (structure) |

BIOLOGICAL EVALUATION

Human Renin Inhibition in vitro

Compound of Formula I were evaluated as inhibitors of human renin in an in vitro assay, as follows: This human renin inhibition test has been previously described in detail [Papaioannou et al., *Clinical and Experimental Hypertension*, A7(9), 1243–1257 (1985)]. Human renin was obtained from the National Institute for Biological Standards, London. An incubation mixture was prepared containing the following components: in a total volume of 0.25 mL: 100 mM Tris-acetate buffer at pH 7.4, 25 ×10$^{-6}$ Goldblatt units of renin, 0.05 mL of plasma from human volunteers taking oral contraceptives, 6.0 mM Na-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at DH 7.4 containing 0.5% BSA to the appropriate concentration. The final concentration of organic solvent in the reaction mixture was less than 1%. Control incubations at 37° C. were used to correct for effects of organic solvent on renin activity. The in vitro enzymatic conversion of angiotensinogen to angiotensin I was inhibited by test compound of the invention as indicated in Table II, below:

TABLE II

| Human Renin in vitro Inhibition Data | |
| --- | --- |
| Compound Example # | IC$_{50}$ Human Renin (nM) |
| Example 1 | 1 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or subdose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I:

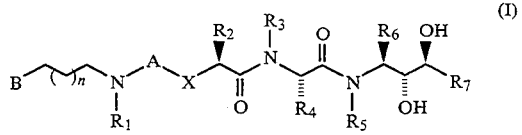

wherein A is selected from CO and SO$_2$; wherein X is selected from oxygen atom and methylene; wherein R$_1$ is selected from hydrido and alkyl; wherein B is a benzo-fused oxazopinyl radical having the structure

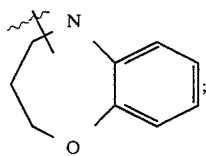

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein R$_2$ is selected from alkyl, cycloalklalkyl, alkylcarbonylaminoalkyl, phenylalkyl and naphthylalkyl, and wherein the cyclic portion of any of said phenylalyl, cycloalkylalkyl and naphthylalkyl groups may be substituted by one or more radicals selected from halo, hydroxy, alkoxy and alkyl; wherein each of R$_3$ and R$_5$ is independently selected from hydrido and alkyl; wherein R$_4$ is selected from

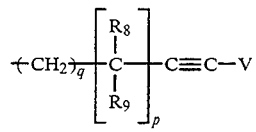

wherein V is selected from hydrido, alkyl, benzyl and phenyl; wherein each of R$_8$ and R$_9$ is a radical independently selected from alkyl, alkenyl and phenyl; wherein R$_6$ is selected from alkyl, cycloalkylalkyl and phenylalkyl, any one of which may be substituted with one or more groups selected from alkyl, hydroxy and alkoxy; wherein R$_7$ is selected from alkyl, cycloalkyl, cycloalkylalkyl, hydroxyalkyl and alkenyl; wherein p is a number selected from zero through five, inclusive; wherein q is a number selected from zero through five, inclusive; and wherein n is a number selected from zero through five, inclusive; or a pharmaceutically-acceptable salt thereof.

2. Compound of claim 1 wherein A is selected from CO and SO$_2$; wherein X is selected from oxygen atom and methylene; wherein R$_1$ is selected from hydrido and alkyl; wherein B is a benzo-fused oxazopinyl radical having the structure

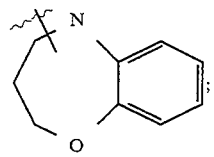

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein R$_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of R$_3$ and R$_5$ is independently selected from hydrido and methyl; wherein R$_4$ is selected from

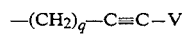
—(CH$_2$)$_q$—C≡C—V wherein V is selected from hydrido and alkyl; wherein R$_6$ is selected from cyclohexylmethyl and phenylmethyl, either one of which may be substituted with one or more groups selected from alkyl, hydroxy and alkoxy; wherein R$_7$ is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

3. Compound of claim 2 wherein A is selected from CO and SO$_2$; wherein X is selected from oxygen atom and methylene; wherein R$_1$ is selected from hydrido, methyl, ethyl, isopropyl and n-propyl; wherein B is a benzo-fused oxazopinyl radical having the structure

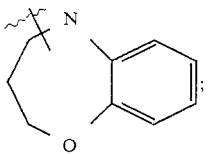

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein $R_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of $R_3$ and $R_5$ is independently selected from hydrido and methyl; wherein $R_4$ is selected from

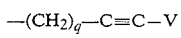

wherein V is selected from hydrido and alkyl; wherein $R_6$ is selected from cyclohexylmethyl and phenylmethyl, either one of which may be substituted with one or more groups selected from alkyl, hydroxy and alkoxy; wherein $R_7$ is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

4. A pharmaceutical composition comprising a therapeutically-effective amount of a renin-inhibiting compound and a pharmaceutically-acceptable carrier or diluent, said renin-inhibiting compound selected from a family of compounds of Formula I:

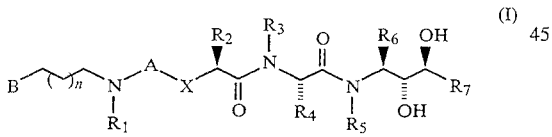

wherein A is selected from CO and $SO_2$; wherein X is selected from oxygen atom and methylene; wherein $R_1$ is selected from hydrido and alkyl; wherein B is a benzo-fused oxazopinyl radical having the structure

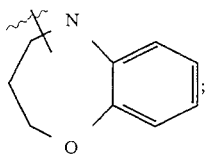

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein $R_2$ is selected from alkyl, cycloalkylalkyl, alkylcarbonylaminoalkyl, phenylalkyl and naphthylalkyl, and wherein the cyclic portion of any of said phenylalkyl, cycloalkylalkyl and naphthylalkyl groups may be substituted by one or more radicals selected from halo, hydroxy, alkoxy and alkyl; wherein each of $R_3$ and $R_5$ is independently selected from hydrido and alkyl; wherein $R_4$ is selected from

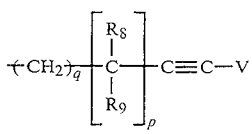

wherein V is selected from hydrido, alkyl, benzyl and phenyl; wherein each of $R_8$ and $R_9$ is a radical independently selected from alkyl, alkenyl and phenyl; wherein $R_6$ is selected from alkyl, cycloalkylalkyl and phenylalkyl, any one of which may be substituted with one or more groups selected from alkyl, hydroxy and alkoxy; wherein $R_7$ is selected from alkyl, cycloalkyl, cycloalkylalkyl, hydroxyalkyl and alkenyl; wherein p is a number selected from zero through five, inclusive; wherein q is a number selected from zero through five, inclusive; and wherein n is a number selected from zero through five, inclusive; or a pharmaceutically-acceptable salt thereof.

5. The composition of claim 4 wherein A is selected from CO and $SO_2$; wherein X is selected from oxygen atom and methylene; wherein $R_1$ is selected from hydrido and alkyl; wherein B is a benzo-fused oxazopinyl radical having the structure

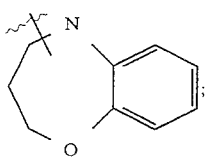

wherein the bond bisected by the wavy; line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein $R_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of $R_3$ and $R_5$ is independently selected from hydrido and methyl; wherein $R_4$ is selected from

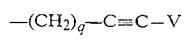

wherein V is selected from hydrido and alkyl; wherein R_6 is selected from cyclohexylmethyl and phenylmethyl, either one of which may be substituted with one or more groups selected from alkyl, hydroxy and alkoxy; wherein R_7 is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

6. The composition of claim 5 wherein A is selected from CO and SO_2; wherein X is selected from oxygen atom and methylene; wherein R_1 is selected from hydrido, methyl, ethyl, isopropyl and n-propyl; wherein B is a benzo-fused oxazopinyl radical having the structure

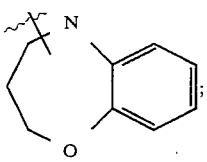

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein R_2 is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of R_3 and R_5 is independently selected from hydrido and methyl; wherein R_4 is selected from

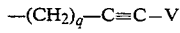
—(CH_2)_q—C≡C—V wherein V is selected from hydrido and alkyl; wherein R_6 is selected from cyclohexylmethyl and phenylmethyl, either one of which may be substituted with one or more groups selected from alkyl, hydroxy and alkoxy; wherein R_7 is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

7. A therapeutic method for treating a circulatory-related disorder, said method comprising administering to a subject susceptible to or afflicted with such disorder a therapeutically-effective amount of a compound of Formula I:

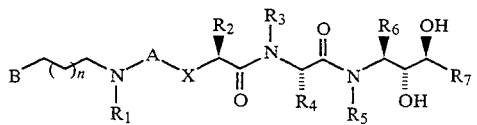

(I)

wherein A is selected from CO and SO_2; wherein X is selected from oxygen atom and methylene; wherein R_1 is selected from hydrido and alkyl; wherein B is a benzo-fused oxazopinyl radical having the structure

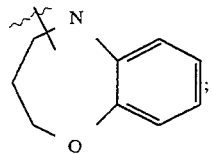

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein R_2 is selected from alkyl, cycloalkylalkyl, alkylcarbonylaminoalkyl, phenylalkyl and naphthylalkyl, and wherein the cyclic portion of any of said phenylalkyl, cycloalkylalkyl and naphthylalkyl groups may be substituted by one or more radicals selected from halo, hydroxy, alkoxy and alkyl; wherein each of R_3 and R_5 is independently selected from hydrido and alkyl; wherein R_4 is selected from

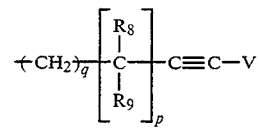

wherein V is selected from hydrido, alkyl, benzyl and phenyl; wherein each of R_8 and R_9 is a radical independently selected from hydrido, alkyl, alkenyl and phenyl; wherein R_6 is selected from alkyl, cycloalkylalkyl and phenylalkyl, any one of which may be substituted with one or more groups selected from alkyl, hydroxy and alkoxy; wherein R_7 is selected from alkyl, cycloalkyl, cycloalkylalkyl, hydroxyalkyl and alkenyl; wherein p is a number selected from zero through five, inclusive; wherein q is a number selected from zero through five, inclusive; and wherein n is a number selected from zero through five, inclusive; or a pharmaceutically-acceptable salt thereof.

8. The method of claim 7 wherein A is selected from CO and SO_2; wherein X is selected from oxygen atom and methylene; wherein R_1 is selected from hydrido and alkyl; wherein B is a benzo-fused oxazopinyl radical having the structure

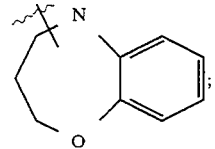

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein $R_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of $R_3$ and $R_5$ is independently selected from hydrido and methyl; wherein $R_4$ is selected from

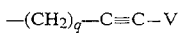

wherein V is selected from hydrido and alkyl; wherein $R_6$ is selected from cyclohexylmethyl and phenylmethyl, either one of which may be substituted with one or more groups selected from alkyl, hydroxy and alkoxy; wherein $R_7$ is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

9. The method of claim 8 wherein A is selected from CO and S02; wherein X is selected from oxygen atom and methylene; wherein $R_1$ is selected from hydrido, methyl, ethyl, isopropyl and n-propyl; wherein B is a benzo-fused oxazopinyl radical having the structure

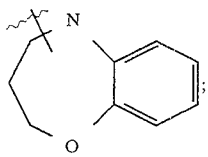

wherein the bond bisected by the wavy line represents a point of attachment of B in Formula I to any attachable position of B, including the nitrogen atom of B, and wherein the bond bisected by the wavy line also represents any substitutable position of B; wherein any substitutable position of B may be substituted with one or more radicals selected from alkyl, alkoxy, alkenyl, alkynyl, halo, trifluoromethyl, oxo, cyano and phenyl, and wherein the ring nitrogen atom of B may be combined with oxygen to form an N-oxide; wherein $R_2$ is selected from cyclohexylmethyl, phenylmethyl and naphthylmethyl, and wherein the cyclic portion of any of said phenylmethyl, cyclohexylmethyl and naphthylmethyl groups may be substituted by one or more radicals selected from halo, hydroxy, alkoxy and alkyl; wherein each of $R_3$ and $R_5$ is independently selected from hydrido and methyl; wherein $R_4$ is selected from

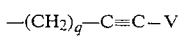

wherein V is selected from hydrido and alkyl; wherein $R_6$ is selected from cyclohexylmethyl and phenylmethyl, either one of which may be substituted with one or more groups selected from alkyl, hydroxy and alkoxy; wherein $R_7$ is selected from alkyl, cycloalkyl and cycloalkylalkyl; wherein q is a number selected from zero through three, inclusive; and wherein n is a number selected from zero through five, inclusive; or a pharmaceutically-acceptable salt thereof.

10. The method of claim 7 wherein said circulatory-related disorder is a cardiovascular disorder.

11. The method of claim 10 wherein said cardiovascular disorder is hypertension.

12. The method of claim 10 wherein said cardiovascular disorder is congestive heart failure.

13. The method of claim 7 wherein said circulatory-related disorder is glaucoma.

14. The method of claim 7 wherein said circulatory-related disorder is renal failure.

* * * * *